(12) United States Patent
Shiraki et al.

(10) Patent No.: US 7,247,231 B2
(45) Date of Patent: Jul. 24, 2007

(54) ANALYZER AND METHOD OF TESTING ANALYZER

(75) Inventors: Yasunori Shiraki, Kyoto (JP); Hideki Nishimura, Kyoto (JP)

(73) Assignee: Arkray, Inc., Kyoto (JP)

( * ) Notice: Subject to any disclaimer, the term of this patent is extended or adjusted under 35 U.S.C. 154(b) by 281 days.

(21) Appl. No.: 10/240,805

(22) PCT Filed: Apr. 6, 2001

(86) PCT No.: PCT/JP01/03014

§ 371 (c)(1),
(2), (4) Date: Oct. 4, 2002

(87) PCT Pub. No.: WO01/77657

PCT Pub. Date: Oct. 18, 2001

(65) Prior Publication Data

US 2003/0057970 A1    Mar. 27, 2003

(30) Foreign Application Priority Data

Apr. 7, 2000    (JP)    ............................. 2000-106133

(51) Int. Cl.
*G01N 27/413*    (2006.01)
(52) U.S. Cl. .................. 205/775; 204/401; 204/406; 204/416; 73/1.02
(58) Field of Classification Search ............... 204/401, 204/406, 403.02, 416; 205/775, 779, 789.5; 73/1.02, 1.03; 324/601, 763
See application file for complete search history.

(56) References Cited

U.S. PATENT DOCUMENTS

| 4,832,817 | A |   | 5/1989  | Uekusa et al. |
|-----------|---|---|---------|---------------|
| 4,882,544 | A |   | 11/1989 | Uekusa et al. |
| 5,405,511 | A | * | 4/1995  | White et al. ............. 205/777.5 |
| 5,438,271 | A | * | 8/1995  | White et al. ................ 324/444 |
| 5,781,024 | A |   | 7/1998  | Blomberg et al. |

FOREIGN PATENT DOCUMENTS

| EP | 0 471 986 | 2/1992 |
|----|-----------|--------|
| EP | 0 537 761 | 4/1993 |
| JP | 6-82113   | 10/1994 |
| JP | 7-111409  | 11/1995 |
| WO | 94/29705  | 12/1994 |

\* cited by examiner

*Primary Examiner*—Kaj K. Olsen
(74) *Attorney, Agent, or Firm*—Hamre, Schumann, Mueller & Larson, P.C.

(57) ABSTRACT

An analyzer measures the concentration of a specific component in a sample liquid supplied to a test piece equipped with first and second terminal parts. An analyzer (X1) includes a stage on which a test piece is placed, a first terminal (40a) for electrical connection with a first terminal part, a second terminal (40b) for electrical connection with a second terminal part, and an electric circuit (6) for measuring parameters required for calculating the concentration of a specific component. A check piece (4'), in place of the test piece, is placed on a stage to test the electric circuit (6). The test of the electric circuit (6) is performed based on a plurality of electric responses from the electric circuit (6) with a plurality of electric conditions applied to the check piece (4').

16 Claims, 15 Drawing Sheets

ANALYZER AND METHOD OF TESTING ANALYZER

This application is a national stage entry of PCT JP01/03014 filed on Apr. 6, 2001.

TECHNICAL FIELD

This invention relates to a device for measuring the concentration of a specific component in a sample liquid, and a method of testing such a device.

BACKGROUND ART

One method for measuring the concentration of a specific component in a sample liquid is a method in which the specific component concentration is computed from the potential difference arising when a reference liquid containing a known concentration of the specific component and a sample liquid containing an unknown concentration of the specific component are electrically shunted.

In this method, by for example setting a plate for concentration measurement relative to the analyzer, the concentration of the specific component is measured. Below, the case in which the concentrations of three types of specific components (for example, $K^+$, $Na^+$, $Cl^-$) in a sample liquid are measured is explained.

The analyzer has, at least, a set portion in which a plate for concentration measurement is set; three pairs of probes (for a total of six); and computation means to compute the concentration of the specific component from the potential differences between each pair of probes.

The plate for concentration measurement has, at least, a reference liquid reception portion, onto which reference liquid is spot-applied; a reference liquid holding portion, which holds the reference liquid; first through third terminal portions, which are in electrical contact with the reference liquid of the reference liquid holding portion; a sample liquid reception portion, into which the sample liquid is spot-applied; a sample liquid holding portion, which holds the sample liquid; fourth through sixth terminal portions, which are in electrical contact with the sample liquid holding portion; and a bridge, which electrically shunts the reference liquid of the reference liquid holding portion and the sample liquid of the sample liquid holding portion.

When the concentration measurement plate is set in the set area of the analyzer, the corresponding probe of the analyzer is in contact with each of the terminal portions. In the analyzer, potential differences between the reference liquid and sample liquid are measured for each specific component, via each probe pair. The computation means of the analyzer computes the concentrations of each specific component based on the potential difference measurement results.

In this analyzer, instead of a concentration measurement plate, a check plate is set in the set portion, and the potential difference measurement electrical circuit is tested for defects. Causes of electrical circuit defects include, for example, malfunctions of electronic parts, breakage in wiring, and contact failure between a probe and the concentration measurement plate (first through sixth terminal portion).

A method of test of the electrical circuit for potential difference measurement is described in, for example, JP-B 6-82113 and in JP-B 7-111409.

The test method described in JP-B 6-82113 employs check plates 9A to 9D, as shown in FIGS. 15 to 18 of this application. Each of these check plates 9A to 9D has a base plate 90 in which are provided a total of six through-holes 90a corresponding to three pairs of probes in the analyzer. On the base plate 90 is stacked a cover plate 92, enclosing conducting layers 91a to 91d. Various configurations for the conducting layers 91a to 91d are shown in FIGS. 15 to 18.

Each of these check plates 9A to 9D is set in the analyzer similarly to a test plate. At this time, each of the probes is in contact with the conducting layers 91a to 91d, so that each of the probe pairs is shunted. Test of the electrical circuit for potential difference measurement is performed by measuring the potential differences between the probe pairs. In this test method, if the potential difference between each probe pair is zero, the electrical circuit for potential difference measurement of the analyzer is judged to be normal, and if not zero, the circuit is judged to be abnormal.

In this test method, measured potentials are always zero, so that it is not possible to test reliably for the presence of defects in the electrical circuit for potential difference measurement. For example, even in a case in which a measurement value corresponding to the actual potential difference cannot be observed due to some abnormality, the measured value for the zero potential in tests is measured as either zero or as a value close to zero. In this case, it is judged that there is no abnormality in the electrical circuit for potential difference measurements. It is also difficult to determine the measurement precision for potentials which deviate greatly from zero potential.

On the other hand, in the test method described in JP-B 7-111409, a check plate 9E such as shown in FIG. 19 is used. This check plate 9E has a base plate 90 in which are provided a total of six through-holes 90a corresponding to the three probe pairs of the analyzer. On this base plate 90 are placed six conducting pads 91e which separately cover each of the through-holes 90a. These conducting pads 91e, together with resistors $R_1$ to $R_3$ and a battery 91f, constitute an electrical circuit as shown in FIG. 20. The conducting pads 91e, resistors $R_1$ to $R_3$, and battery 91f are enclosed by the frame 92 positioned on the base plate 90. The space enclosed by the frame 92 is sealed with resin.

With the probes brought into contact with the conducting pads 91e in the check plate 9E, a voltage is applied across each of the probe pairs by the battery 91f. The voltage value for each probe pair is measured, and the electrical circuit for potential difference measurement is tested for defects.

In this test method, a voltage is applied to each of the probe pairs by the battery 91f incorporated into the check plate 9E, so that the precision of the output of the battery 91f necessarily has an effect on the test results. The battery output is not strictly constant; in particular, if consumption exceeds a certain capacity, the output gradually declines. Hence a method which employs a battery 91f cannot be regarded as appropriate in order to maintain test precision. Moreover, it is difficult to make the output of the battery 91f incorporated into the check plate 9E variable. Consequently a given check plate 9E can only perform tests using a single reference potential, and so there is the drawback that, similarly to test methods described in the previous publications, defects in an electrical circuit for potential difference measurement cannot be reliably detected.

DISCLOSURE OF THE INVENTION

A first aspect of this invention provides an analyzer for measuring a concentration of a specific component in a sample liquid supplied to the test piece with use of a test piece which has a first terminal portion and a second terminal portion, the analyzer comprising a set portion in which the test piece is set, a first measurement terminal for electrical connection to the first terminal portion and a second measurement terminal for electrical connection to the second terminal portion, and a measurement electrical circuit to measure parameters necessary to compute the concentration of the specific component; the analyzer further comprising test means to test the measurement electrical circuit using a check piece instead of the test piece; wherein the test means applying a plurality of electrical conditions to the check piece for testing the measurement electrical circuit based on a plurality of electrical responses obtained from the measurement electrical circuit when the electrical conditions are applied individually.

In a preferred embodiment, the test means is designed to test the measurement electrical circuit by comparing each of the electrical responses with an ideal electrical response for each of the electrical conditions.

In a preferred embodiment, the analyzer is designed to measure the potential difference occurring between a reference liquid having a known concentration of the specific component, and a sample liquid having an unknown concentration of the specific component.

In this case, the check piece used has a first conducting portion for contact with the first measurement terminal and a second conducting portion for contact with the second measurement terminal. When the check piece is not set in the set portion, the first conducting portion and the second conducting portion are insulated from each other.

As the plurality of electrical conditions, for example, a plurality of standard voltages are set. The plurality of standard voltages are, for example, at least two voltages selected from among positive values, zero, and negative values.

It is preferable that at least one among the plurality of standard voltages be applied by supplying a voltage from the power supply to the first conducting portion, while grounding the second conducting portion. The voltage of the power supply is, for example, controlled using a regulator within the analyzer.

In a preferred embodiment, the measurement electrical circuit is designed such that the current value is measured when a constant voltage is applied across the first terminal portion and the second terminal portion.

In this case, the check piece used has a first conducting portion for contact with the first measurement terminal and a second conducting portion for contact with the second measurement terminal. The first conducting portion and the second conducting portion are electrically connected.

As the plurality of electrical conditions, for example, a plurality of standard currents are set. The plurality of standard currents include, for example, positive values and zero.

In a preferred embodiment, the measurement electrical circuit has a response measurement instrument which measures the electrical response, and is designed to apply an electrical condition to the response measurement instrument and calibrate the response measurement instrument.

When testing the measurement electrical circuit, the check plate may be incorporated from outside the device, or may be incorporated into the device interior in advance.

A second aspect of this invention provides a method of testing an analyzer for measuring a concentration of a specific component in a sample liquid supplied to a test piece having a first terminal portion and a second terminal portion; the analyzer comprising a set portion in which the test piece is set, a first measurement terminal for electrical connection to the first terminal portion, a second measurement terminal for electrical connection to the second terminal portion, and a measurement electrical circuit which measures parameters necessary to compute the concentration of the specific component, the method comprising: a first step for applying an electrical condition to the check piece; a second step for measuring an electrical response obtained from the measurement electrical circuit when the electrical condition is applied; and a third step for comparing the electrical response with an ideal electrical response obtainable when the electrical condition is applied to the check piece; wherein the first through third steps are performed separately for each of a plurality of electrical conditions.

In a preferred embodiment, the measurement electrical circuit has a response measurement instrument to measure the electrical response, and a step is included in which, prior to the first step, an electrical condition is applied to the response measurement instrument, and the response measurement instrument is calibrated.

As the plurality of electrical conditions, a plurality of standard voltages, or a plurality of standard currents, are set.

BEST MODE FOR CARRYING OUT THE INVENTION

Figure 1:
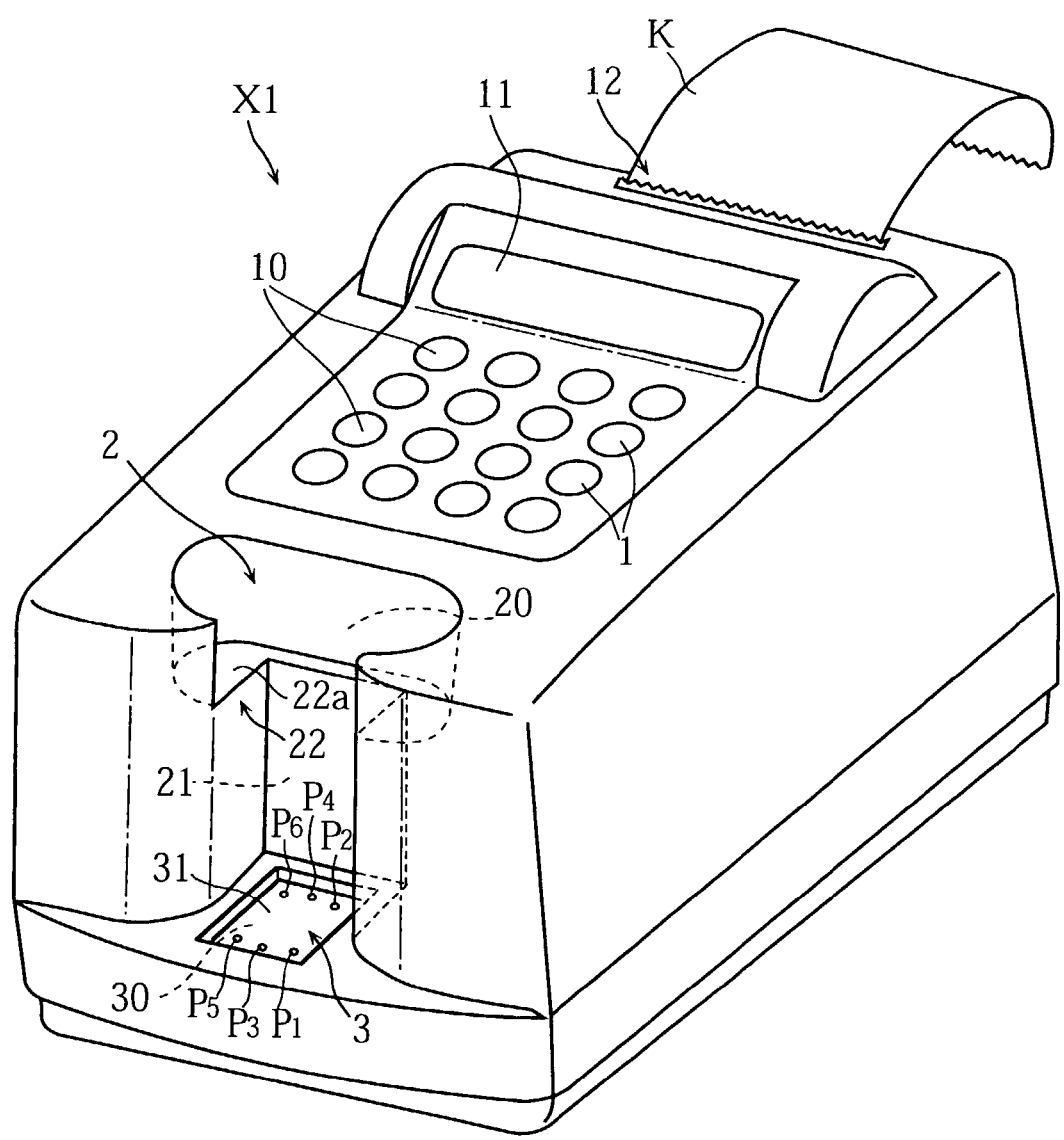
FIG. 1 is an overall perspective view showing one example of an analyzer of a first embodiment of the invention.

The analyzer X1 of a first embodiment of this invention, shown in FIG. 1, electrochemically measures the concentration of a specific component in a sample liquid through comparison with a reference liquid containing a known concentration of the specific component.

The sample liquid may be, for example, blood, urine, saliva, or other biological samples, or liquids obtained by adjusting same. Specific components may be, for example, $Na^+$, $K^+$, or $Cl^-$.

On the upper face of the analyzer X1 are provided various operation buttons 10, a display 11 which displays measurement results and operating conditions, and a discharge portion 12 which discharges recording paper K. On the front face of the analyzer X1 is provided a pipette holder 2. On the bottom of the pipette holder 2 is provided a set portion 3, in which is set a potential difference measurement plate 4 (see FIG. 4 through FIG. 6).

Figure 2:
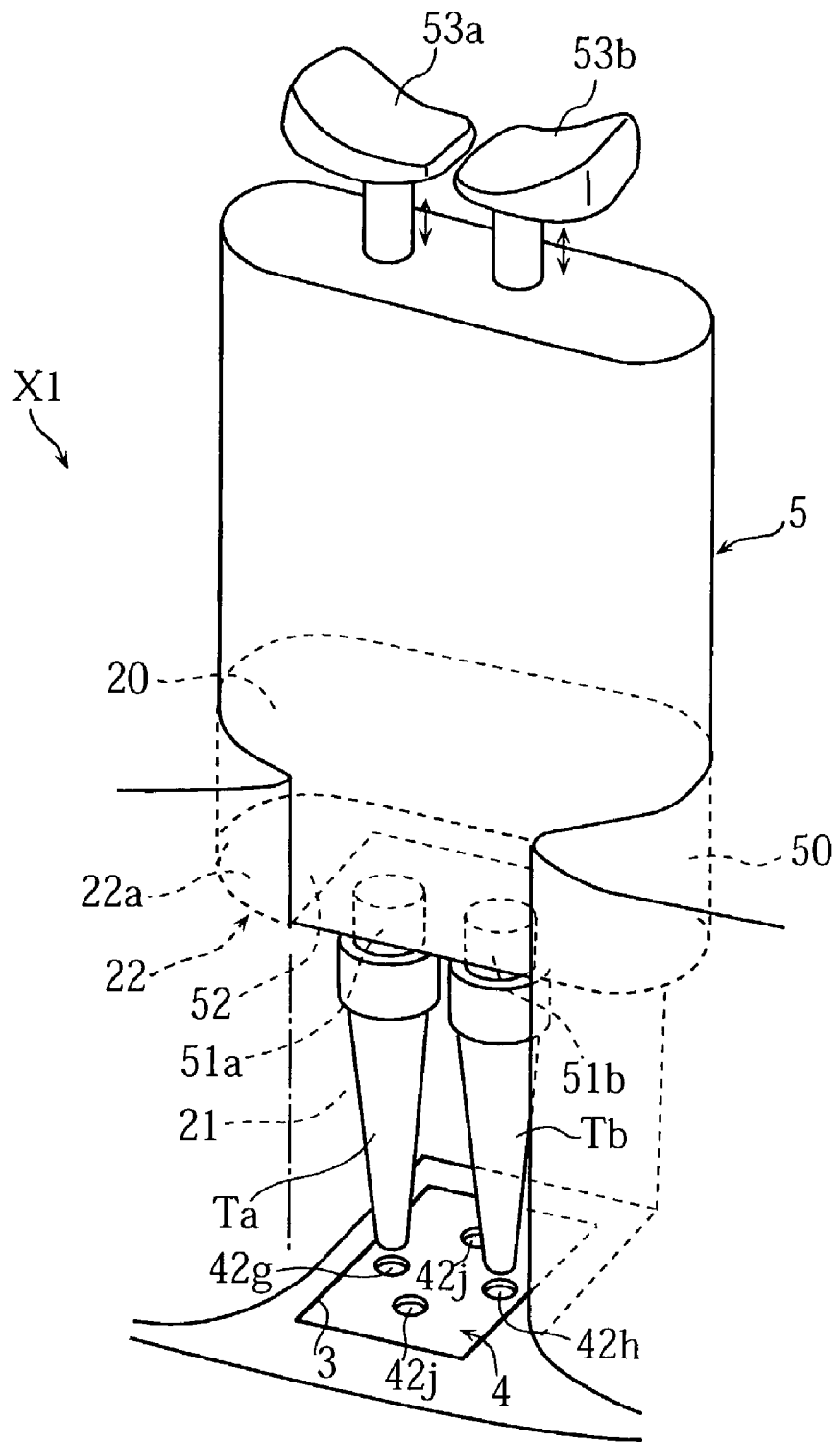
FIG. 2 is an enlarged perspective view of principal components, showing the configuration in the vicinity of the pipette holder in the analyzer of FIG. 1.

The pipette holder 2 has a first space 20 which is penetrated vertically and open in the forward direction, and a second space 21 which is connected with the first space 20 below the first space 20, and is open in the forward direction, as shown in FIG. 1 and FIG. 2. The body portion 50 of the pipette 5 is accommodated by the first space 20, and the tip portions 51a, 51b of the pipette 5 as well as the tips Ta, Tb mounted on these portions are accommodated by the second space 21. A step 22 is formed between the first space 20 and second space 21. The bottom face 52 of the body portion 50 of the pipette 5 catches on the upper face 22a of this step 22.

The pipette 5 shown in FIG. 2 is a double pipette. In this pipette 5, by moving the operating portions 53a, 53b up and down, a prescribed quantity of liquid can be sucked in or discharged via the tip apertures of the tips Ta, Tb.

Figure 3:
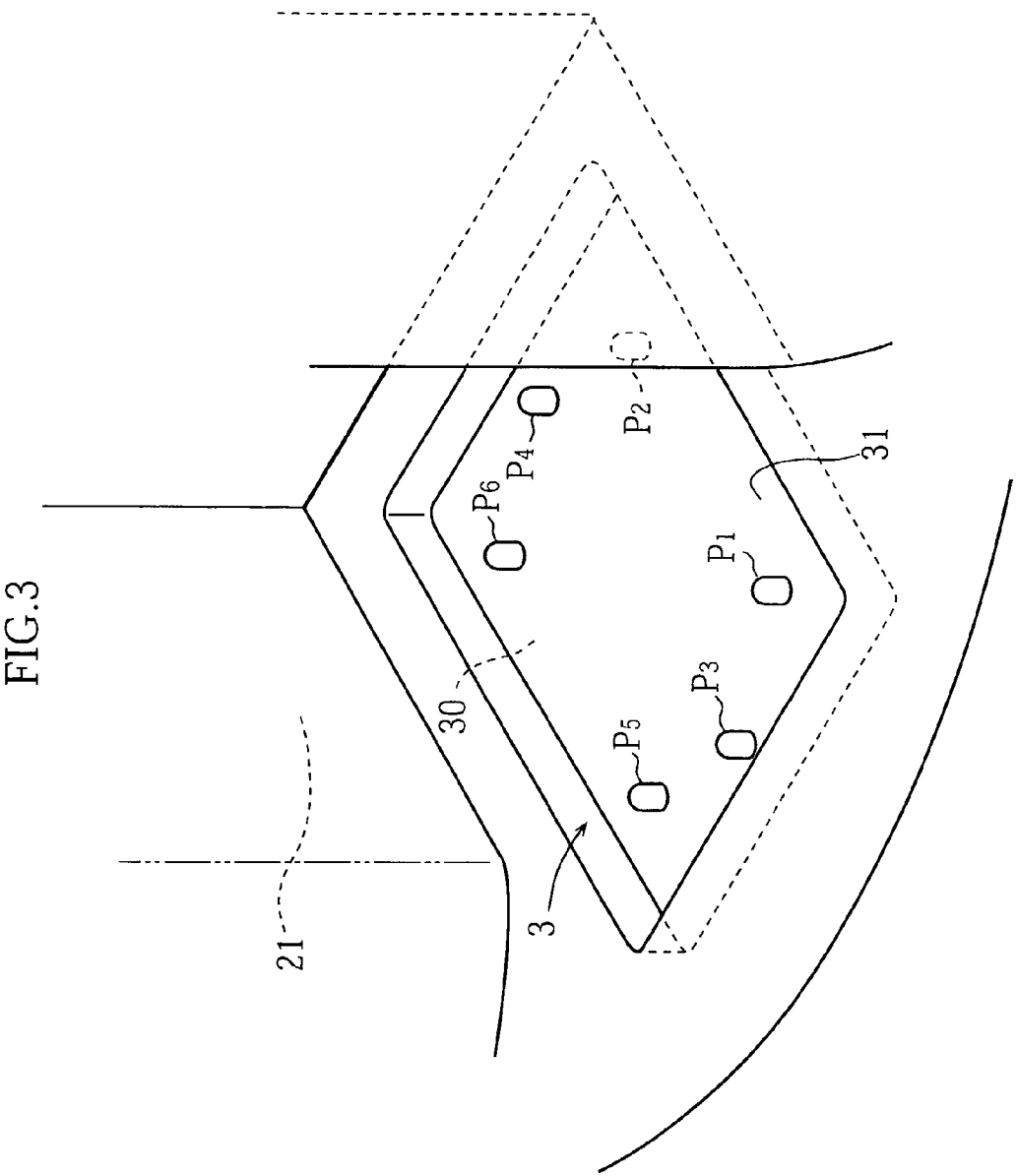
FIG. 3 is an enlarged perspective view of principal components, showing the configuration in the vicinity of the set portion in which the potential difference measurement plate (test piece) is set in the analyzer of FIG. 1.

The set portion 3 has an accommodating space 30 capable of holding a potential difference measurement plate 4 (see FIG. 4 through FIG. 6), as shown in FIG. 3. Three pairs (for a total of six) of probes $P_1$ through $P_6$ protrude upward from the bottom face 31 of this set portion 3. In the analyzer X1, the potential differences arising from differences in concentration of, for example, $K^+$, $Na^+$, or $Cl^-$ between a reference liquid and a sample liquid are measured through these probe pairs $P_1$ to $P_6$.

Figure 4:
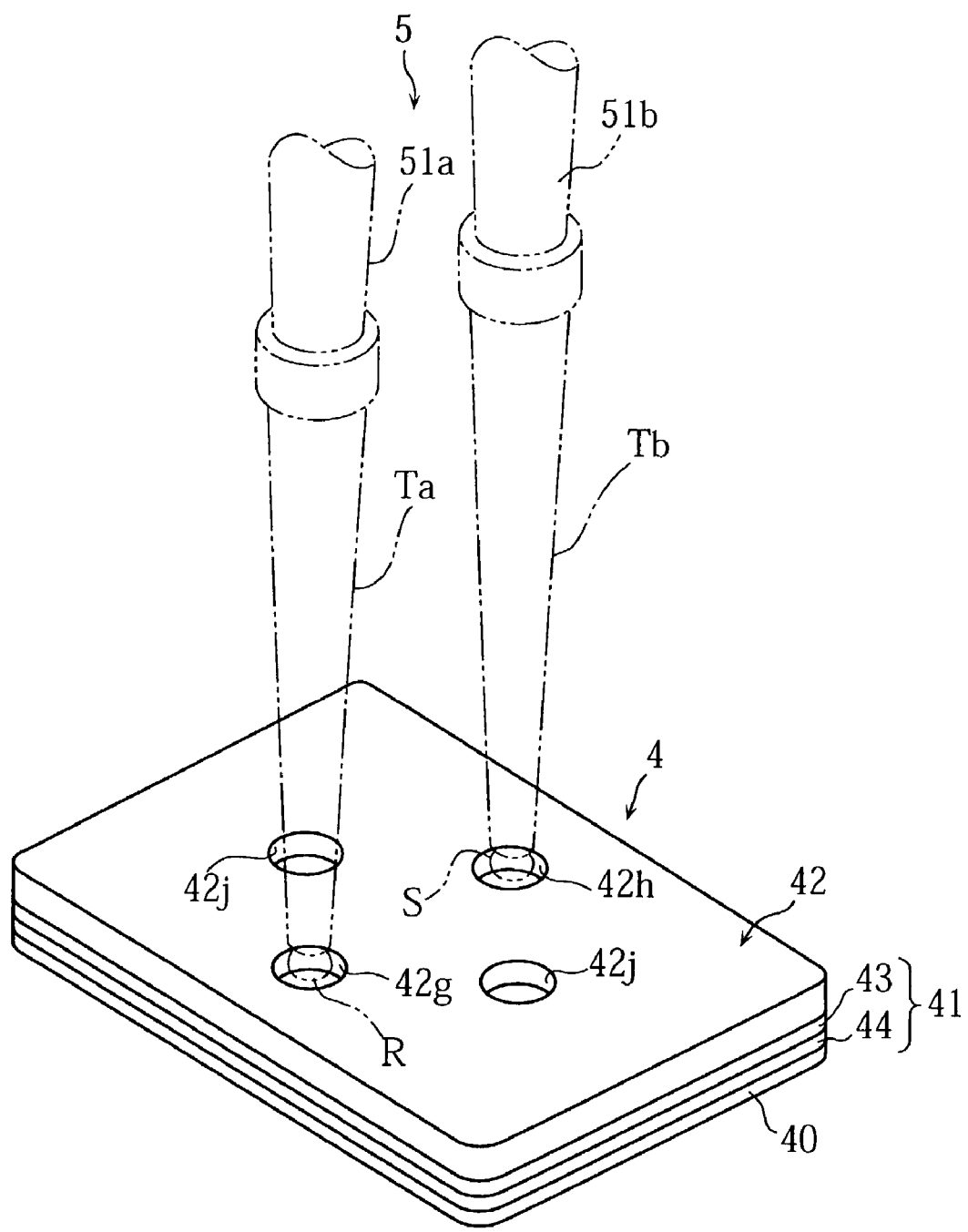
FIG. 4 is an overall perspective view, seen from the top surface side, of a potential difference measurement plate.
Figure 5:
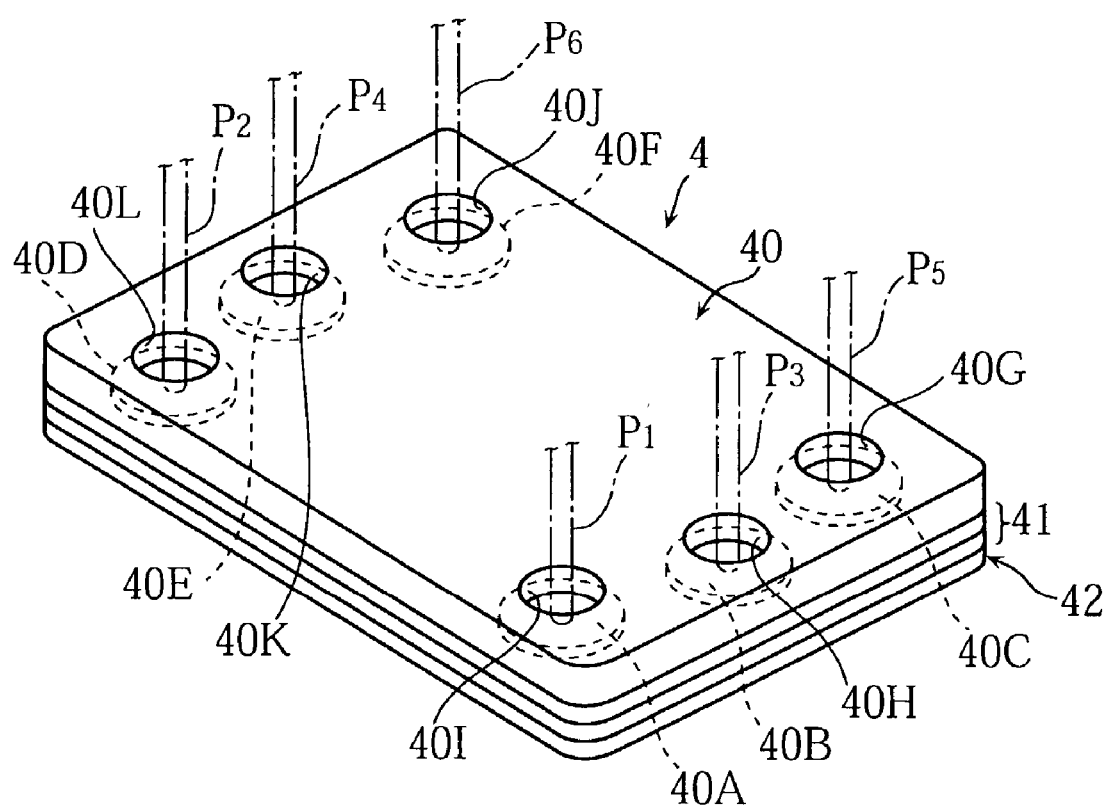
FIG. 5 is an overall perspective view, seen from the rear surface side, of a potential difference measurement plate.
Figure 6:
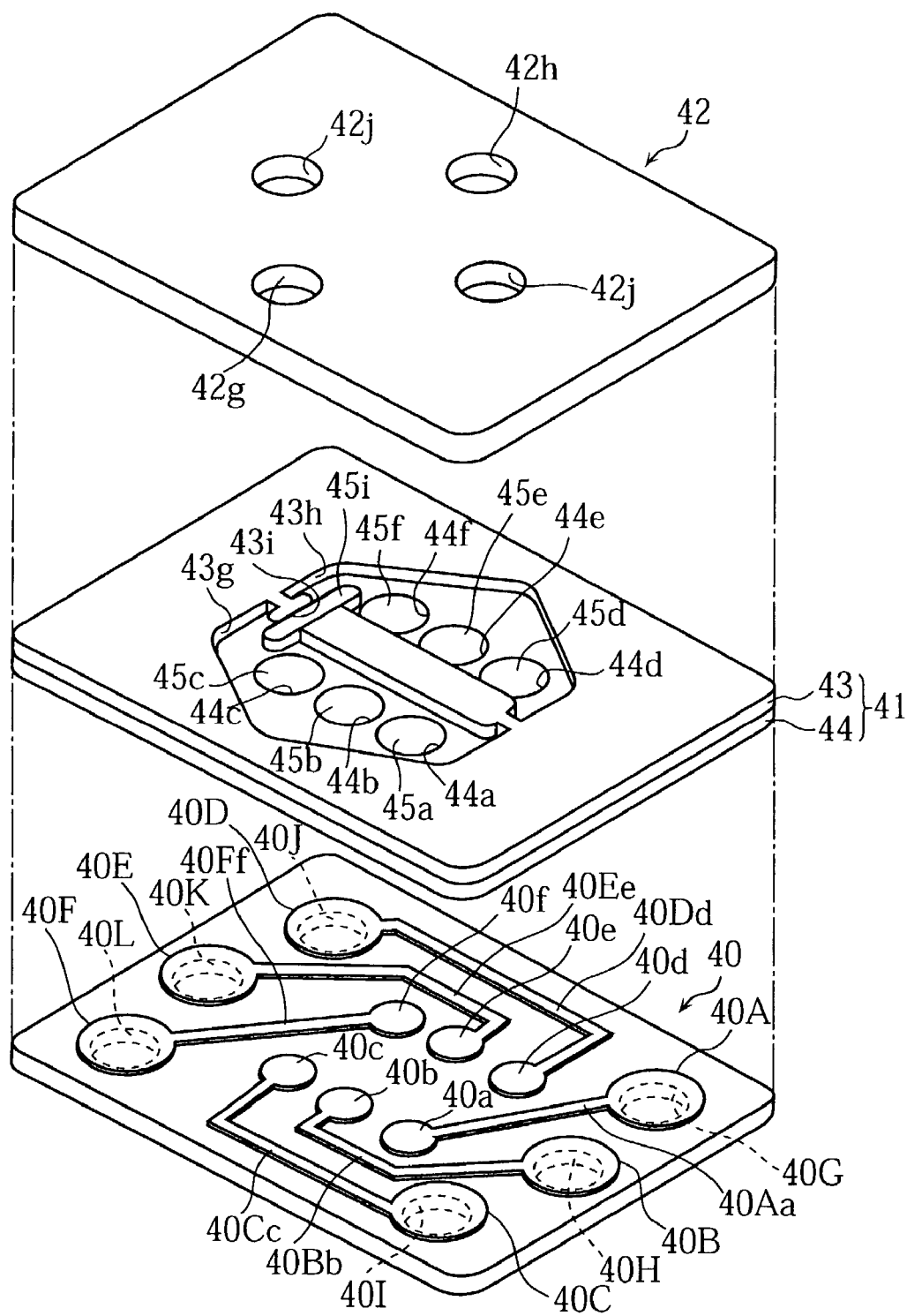
FIG. 6 is an exploded perspective view of a potential difference measurement plate.

The potential difference measurement plate 4 is formed by stacking a resist layer 41 and cover film 42 onto a base film 40, as shown in FIG. 4 through FIG. 6. The potential difference measurement plate 4 is configured so as to enable measurement of potential differences for three types of ions, for example $Na^+$, $K^+$, and $Cl^-$.

The base film layer 40 is electrically insulating. The base film layer 40 has a rectangular shape overall.

Three terminals each, 40A to 40C and 40D to 40F, are formed on the two short edges of the base film layer 40. Each of the three sets of terminals 40A to 40C and 40D to 40F is arranged in the direction of the shorter edges of the base film layer 40. Through-holes 40G, 40H, 40I, 40J, 40K, 40L are formed corresponding to the terminals 40A to 40F at the two shorter edges of the base film layer 40. By means of the through-holes 40G to 40L, the corresponding terminals 40A to 40F are exposed. The probes $P_1$ to $P_6$ are in contact with the terminals 40A to 40F via the corresponding through-holes 40G to 40L.

Six liquid-receiving pads 40a to 40f are formed in the center portion of the base film layer 40. Specific components of the reference liquid or sample liquid are supplied to these liquid-receiving pads 40a to 40f. Each of the liquid-receiving pads 40a to 40f is electrically connected to the corresponding terminals 40A to 40F via the conducting wires 40Aa, 40Bb, 40Cc, 40Dd, 40Ee, 40Ff.

The resist film layer 41 comprises a first resist film layer 43, and a second resist film layer 44. The first resist film layer 43 and second resist film layer 44 are electrically insulating. The first resist film layer 43 and second resist film layer 44 have a rectangular shape overall.

Six connecting holes 44a to 44f are formed in the center portion of the second resist film layer 44. An ion selection film 45a to 45f is inserted into each of the connecting holes 44a to 44f. The ion selection films 45a, 45d selectively pass, for example, $K^+$. The ion selection films 45b, 45e selectively pass, for example, $Cl^-$. The ion selection films 45c, 45f selectively pass, for example, $Na^+$.

A reference liquid holding hole 43g and sample liquid holding hole 43h are formed in the center portion of the first resist film 43. The reference liquid holding hole 43g is connected to the three connecting holes 44a, 44b, 44c; the sample liquid holding hole 43h is connected to the three connecting holes 44d, 44e, 44f. The reference liquid holding hole 43g and sample liquid holding hole 43h are connected via a cutout 43i. A bridge 45i permitting the movement of ions is positioned in this cutout 43i.

A reference liquid receiving aperture 42g and sample liquid receiving aperture 42h are formed in the center portion of the long side of the cover film layer 42. The reference liquid receiving aperture 42g is connected to the reference liquid holding hole 43g of the first resist film layer 43. The sample liquid receiving aperture 42h is connected to the sample liquid holding hole 43h of the first resist film 43. Two air vent holes 42j are formed in the cover film layer 42. Each of the air vent holes 42j is connected to both the reference liquid holding hole 43g and to the sample liquid holding hole 43h.

In actual potential difference measurements, as shown in FIG. 2, first the potential difference measurement plate 4 is set in the set portion 3, and a pipette 5 is held by the pipette holder 2.

The potential difference measurement plate 6 is set such that the reference liquid receiving aperture 42g and sample liquid receiving aperture 42h are opened upward. In this state, the terminals 40A to 40F of the potential difference measurement plate 4 are in contact with the corresponding probes $P_1$ to $P_6$, as shown in FIG. 5.

On the other hand, tips Ta, Tb are mounted on the tip portions 51a, 51b of the pipette 5 as shown in FIG. 2. Then, the reference liquid or sample liquid is drawn into the tips Ta, Tb by operating the operating portions 53a, 53b. The pipette 5 is held by the pipette holder 2 by catching the bottom face 52 of the body portion 50 on the upper face 22a of the step 22 of the pipette holder 2.

Next, the operating portions 53a, 53b of the pipette 5 are moved downward, to dispense the reference liquid R and sample liquid S from the tip apertures of the tips Ta, Tb respectively, as shown in FIG. 4. By this means, the reference liquid is spot-applied to the reference liquid receiving aperture 42g, and the sample liquid is spot-applied to the sample liquid receiving aperture 42h.

As is clear from FIG. 6, the reference liquid R which is spot-applied from the reference liquid receiving aperture 42$g$ is held by the reference liquid holding hole 43$g$, and the sample liquid S which is spot-applied from the sample liquid receiving aperture 42$h$ is held by the sample liquid holding hole 43$h$. Because the reference liquid holding hole 43$g$ and sample liquid holding hole 43$h$ are connected via a cutout 43$i$ in which a bridge 45$i$ is positioned, the reference liquid R and sample liquid S are electrically shunted.

The $K^+$, $Cl^-$ and $Na^+$ ions in the reference liquid R held in the reference liquid holding hole 43$g$ pass through the ion selection membranes 45$a$, 45$b$, 45$c$ respectively, to reach the reference liquid-receiving pads 40$a$, 40$b$, 40$c$. The $K^+$, $Cl^-$ and $Na^+$ ions in the sample liquid S held in the sample liquid holding hole 43$h$ pass through the ion selection membranes 45$d$, 45$e$, 45$f$ respectively, to reach the sample liquid-receiving pads 40$d$, 40$e$, 40$f$. As a result, potential differences occur between the reference liquid-receiving pads 40$a$, 40$b$, 40$c$ and the sample liquid-receiving pads 40$d$, 40$e$, 40$f$, respectively, arising from the differences in concentration of $K^+$, $Cl^-$ or $Na^+$ in the reference liquid R and the concentrations of the same ions in the sample liquid S.

Figure 7:
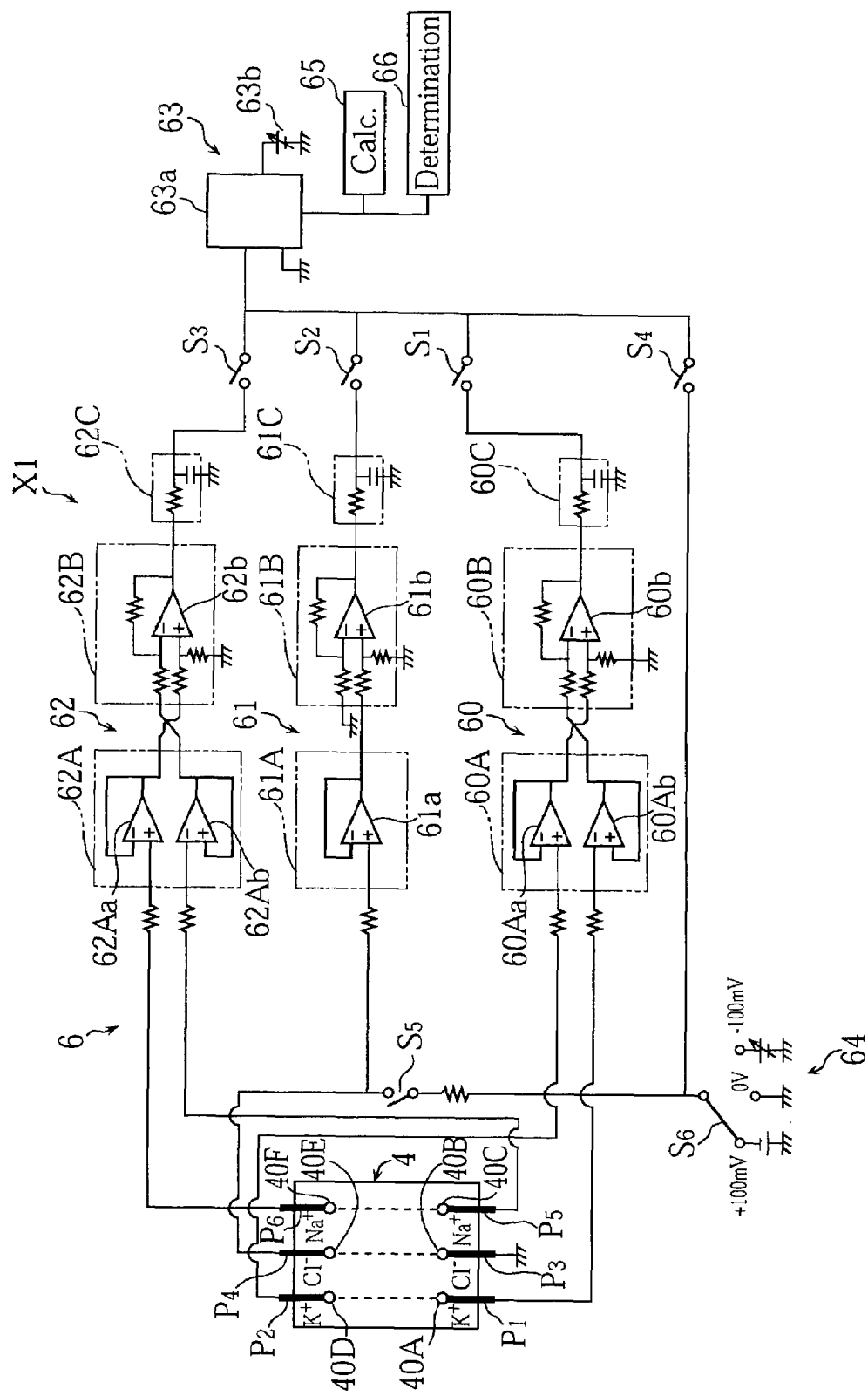
FIG. 7 is a schematic view showing mainly the potential difference measurement circuit, when the potential difference measurement plate of FIG. 4 through FIG. 6 is set in the analyzer of FIG. 1.

This potential difference is measured by the potential difference measurement electrical circuit 6 shown in FIG. 7, via the three pairs of probes $P_1$ to $P_6$ As shown in FIG. 5, the potential difference arising from the difference in concentration of $K^+$ is measured by bringing the probes $P_1$, $P_2$ into contact with the terminals 40A, 40D. The potential difference arising from the difference in concentration of $Cl^-$ is measured by bringing the probes $P_3$, $P_4$ into contact with the terminals 40B, 40E. The potential difference arising from the difference in concentration of $Na^+$ is measured by bringing the probes $P_5$, $P_6$ into contact with the terminals 40C, 40F.

As shown in FIG. 7, the potential difference measurement circuit 6 has a $K^+$ measurement circuit 60, $Cl^-$ measurement circuit 61, $Na^+$ measurement circuit 62, potential difference measurement instrument 63, power supply 64, computation portion 65, determination portion 66, and a plurality of analog switches $S_1$ to $S_6$.

The $K^+$ measurement circuit 60, $Cl^-$ measurement circuit 61, and $Na^+$ measurement circuit 62 have an impedance-matching system 60A, 61A, 62A, differential system 60B, 61B, 62B, and a low-pass filter 60C, 61C, 62C.

The impedance-matching systems 60A, 62A of the $K^+$ measurement circuit 60 and $Na^+$ measurement circuit 62 amplify the inputs from the probes $P_1$, $P_2$, $P_5$, $P_6$, and have a pair of impedance-matching amplifiers 60Aa, 60Ab, 62Aa, 62Ab. The $Cl^-$ measurement circuit 61 amplifies the input from the probes $P_3$, $P_4$, and as the probe $P_3$ is grounded, the impedance-matching system 61A has a single impedance-matching amplifier 61$a$.

The differential systems 60B, 61B, 62B have differential amplifiers 60$b$, 61$b$, 62$b$ which differentiate the outputs from the amplifiers 60Aa, 60Ab, 61$b$, 62Aa, 62Ab of the impedance-matching systems 60A, 61A, 62A. In the $Cl^-$ measurement circuit 61, because there is one impedance-matching amplifier 61$a$ in the impedance-matching system 61A, one of the inputs to the differential amplifier 61$b$ is zero.

The low-pass filters 60C, 61C, 62C reduce the noise components, and each have a resistor and a capacitor.

The potential difference measurement instrument 63 has, for example, an A/D converter 63$a$ capable of potential difference measurement, and a knob-operated regulator 63$b$ which calibrates this A/D converter 63$a$.

The voltage of the power supply 64 is controlled by a regulator within the equipment. This power supply 64 is designed to be able to supply three types of voltage (standard voltages), 100 mV, 0 mV, and −100 mV, to the probe $P_4$ by switching an analog switch $S_6$.

The computation portion 65 computes the concentration of a specific component based on the potential difference measured by the A/D converter 63$a$. This computation portion 65 has, for example, a CPU, ROM, and RAM. Working curve data indicating the relation between the concentration of each specific component and the potential difference, and a program to compute the concentration of a specific component by applying measured potential differences to the working curve data, are stored in the ROM. The working curve data is created based on, for example, the Nernst equation.

The determination portion 66 judges whether there is a defect in the potential difference measurement circuit 6. This determination portion 66 has, for example, a CPU, ROM, and RAM. Ideal response voltage values for each standard voltage, and a program which compares response voltage values actually measured by the A/D converter 63$a$ at each standard voltage and judges whether there is a defect in the potential difference measurement circuit 6, for example, are stored in the ROM.

The computation portion 65 and determination portion 66 may be configured so as to share the CPU and RAM.

Each of the measurement circuits 60, 61, 62 can be separately driven and powered by turning on and off the plurality of analog switches $S_1$ through $S_6$.

In the potential difference measurement circuit 6, potential difference measurements for $K^+$, $Cl^-$, or $Na^+$ are performed as follows.

First, the analog switch $S_1$ is closed, and the analog switches $S_2$, $S_3$, $S_4$, and $S_5$ are opened. In this state, the output from the probes $P_1$, $P_2$ is input to each of the amplifiers 60Aa, 60Ab of the impedance-matching system 60A, and is amplified. The outputs from the amplifiers 60Aa, 60Ab are differentiated by the differentiating amplifier 60$b$. This difference is equivalent to the difference in inputs (potential difference) from the probes $P_1$, $P_2$. The potential difference is measured in the potential difference measurement instrument 63 after passing through the low-pass filter 60C.

Similarly, by closing the analog switch $S_2$ while opening the analog switches $S_1$, $S_3$, $S_4$, $S_5$, the potential difference equivalent to the input difference between the probes $P_3$, $P_4$ is measured in the potential difference measurement instrument 63. The input difference (potential difference) between the probes $P_5$, $P_6$ is measured in the potential difference measurement instrument 63 by closing only the analog switch $S_3$.

The concentrations of specific components are computed by the computation portion 65 from the potential difference measurement results. The computation results are displayed, for example, on the display 11. The computation results can be printed onto recording paper K discharged from the discharge portion 12 by operation of an appropriate operating button (see FIG. 1). Of course, the measurement results can also be recorded onto an IC card, floppy disk, or other recording media.

Figure 8:
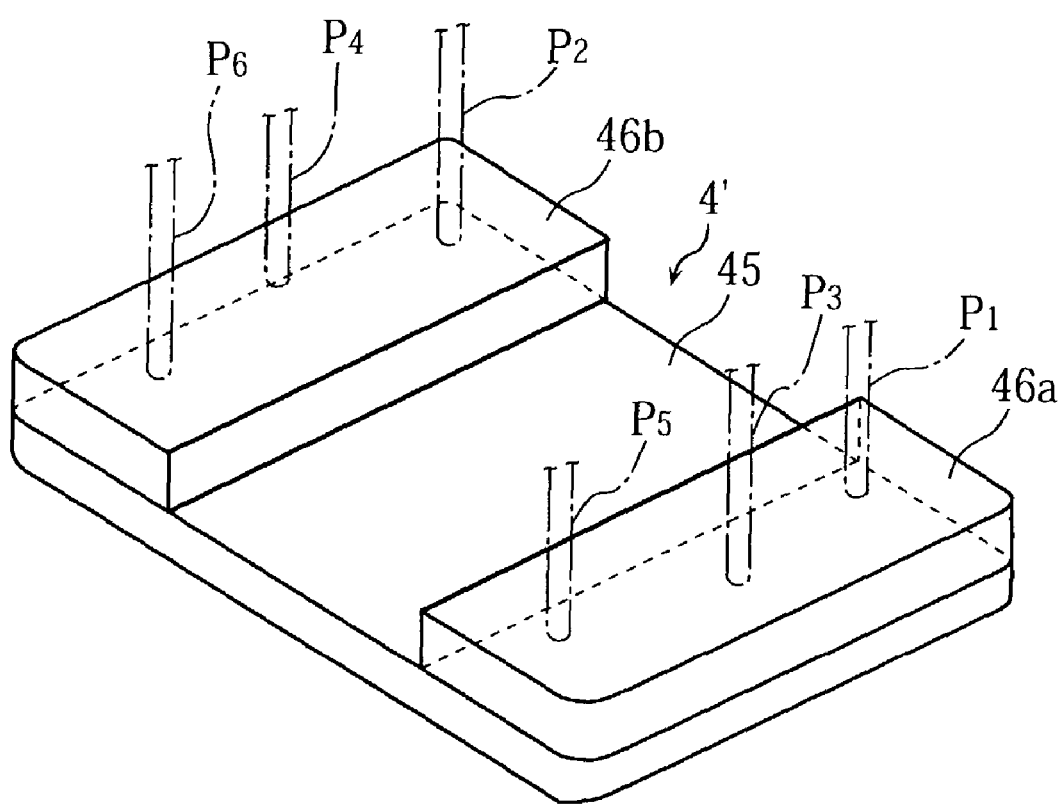
FIG. 8 is an overall perspective view of a check plate (check piece) used when testing a potential difference measurement circuit.

By using the check plate 4' shown in FIG. 8 in the analyzer X1, the potential difference measurement circuit 6 can be tested for defects. Possible defects in the potential difference measurement circuit 6 include damage to electronic components comprised by the circuit; wire breakage; and contact failure of the probes $P_1$ to $P_6$ with the check plate 4' (potential measurement plate 4).

The check plate 4' has a base member 45 and two conducting portions 46a, 46b. The base member 45 is formed into a rectangular shape from a material with highly insulating properties (for example, a resistance value of $10^{11}$ Ω or higher) Each of the conducting portions 46a, 46b is positioned at a short edge of the base member 45. Hence the conducting portions 46a, 46b are insulated from each other.

Figure 9:
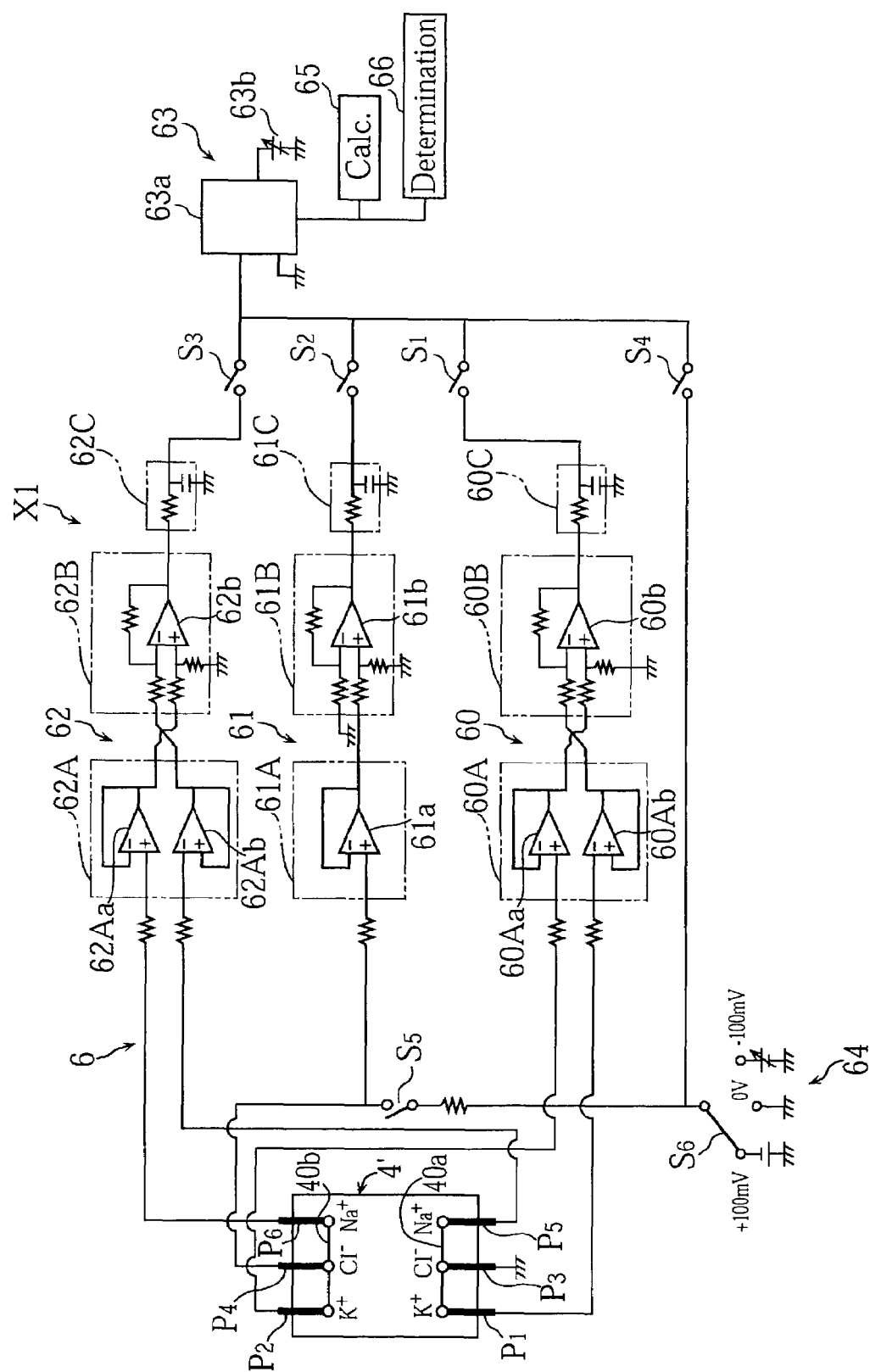
FIG. 9 is a schematic view mainly showing a potential difference measurement circuit when a check plate is set in the analyzer of FIG. 1.

This check plate 4' is formed such that the plane-view area of the base member 45 corresponds to the area of the bottom face 31 of the set portion 3 (see FIGS. 1 and 2) of the analyzer X1, and the total thickness of the base member 45 and the conducting portions 46a, 46b corresponds to the thickness of the set portion 3. Hence similarly to the case of the potential difference measurement plate 4, the check plate 4' is entirely accommodated by the set portion 3. At this time, if the check plate 4' is set in the set portion 3 with the conducting portions 46a, 46b on the lower side, the conducting portions 46a, 46b each are in contact with the probes $P_1$ to $P_6$. In this state, the probes $P_1$, $P_3$, $P_5$, and the probes $P_2$, $P_4$, $P_6$, are respectively electrically connected, and the potential difference measurement circuit 6 is configured as shown in FIG. 9.

In the potential difference measurement circuit 6, the probe $P_3$ for input to the Cl⁻ measurement circuit 61 is grounded, and by turning on the analog switch $S_5$, power from the power supply 64 is supplied to the probe $P_4$. As explained, three types of standard voltages, +100 mV, 0V, and −100 mV, can be supplied to the probe $P_4$ from the power supply 64. Consequently the potential difference measurement circuit 6 can be tested using three types of standard voltage. Also, by turning off the analog switches $S_4$, $S_5$, three types of voltage can be supplied directly to the A/D converter 63a from the power supply 64.

Tests using +100 mV are performed with the switch $S_6$ connected to the +100 mV terminal. First only the analog switch $S_4$ is closed, and the value is measured using the A/D converter 63a. If the measured value deviates from +100 mV, the knob-operated regulator 63b is used to calibrate the A/D converter 63a such that the measurement value is +100 mV.

Next, the analog switch $S_4$ is opened, and the analog switch $S_5$ is closed. The probes $P_2$, $P_4$, $P_6$ are shunted via the conducting portion 46b, so that the voltage from the power supply 64 is input, via the probe $P_4$, to the K⁺ measurement circuit 60 and the Na⁺ measurement circuit 62 from the probes $P_2$, $P_6$.

If the analog switch $S_1$ is closed and the analog switches $S_2$, $S_3$ are opened, the input from the probe $P_2$ is input to the impedance-matching amplifier 60Aa of the impedance-matching system 60A and is amplified. On the other hand, zero voltage is input to the impedance-matching amplifier 60Ab through the probe $P_1$ shunted to the grounded probe $P_3$, and is amplified. The outputs from the impedance-matching amplifiers 60Aa, 60Ab are differentiated by the differentiating system 60B, and a level equivalent to the input difference (potential difference) is output. The output from the differentiating system 60B is subjected to noise reduction via the low-pass filter 60C, and is output from the low-pass filter 60C. The output from the low-pass filter 60C is measured by the A/D converter 63a.

The A/D converter 63a has previously been calibrated to +100 mV, and a voltage of +100 mV is applied across the probes $P_1$, $P_2$. Hence if the K⁺ measurement circuit 60 is normal, and there is no contact failure between the probes $P_1$ to $P_4$ and the check plate 4', the value measured by the A/D converter 63a is +100 mV. On the other hand, if the value measured by the potential difference measurement instrument 63 is shifted upward a fixed amount from +100 mV, then either there is an abnormality in the K⁺ measurement circuit 60, or else contact failure between the probes $P_1$ to $P_4$ and the check plate 4' has occurred.

If the analog switch $S_3$ is closed and the analog switches $S_1$, $S_2$, $S_4$ are opened, then an test can be performed to determine, from the measured value of the A/D converter 63a, whether there is a defect in the Na⁺ measurement circuit 62, or whether contact failure occurs at the probes $P_3$ to $P_6$. On the other hand, the Cl⁻ measurement circuit 61 is tested via the check plate 4' by closing the analog switches $S_2$, $S_5$ and opening the analog switches $S_1$, $S_3$, $S_4$.

The potential difference measurement instrument 63 has already been calibrated at +100 mV in the test of the K⁺ measurement circuit 60, and so there is no need to repeat this calibration in tests of the Na⁺ measurement circuit 62 and the Cl⁻ measurement circuit 61.

Then, tests are performed at 0V and at −100 mV. These tests are substantially similar to the test at +100 mV explained. For example, after performing calibration of the potential difference measurement instrument 63, the analog switches $S_1$ to $S_6$ are switched appropriately, and test of the K⁺ measurement circuit 60, test of the Na⁺ measurement circuit 62, and test of the Cl⁻ measurement circuit 61 are performed in sequence.

Next, the analyzer of a second embodiment of the invention is explained, referring to FIG. 10 through FIG. 14.

Figure 10:
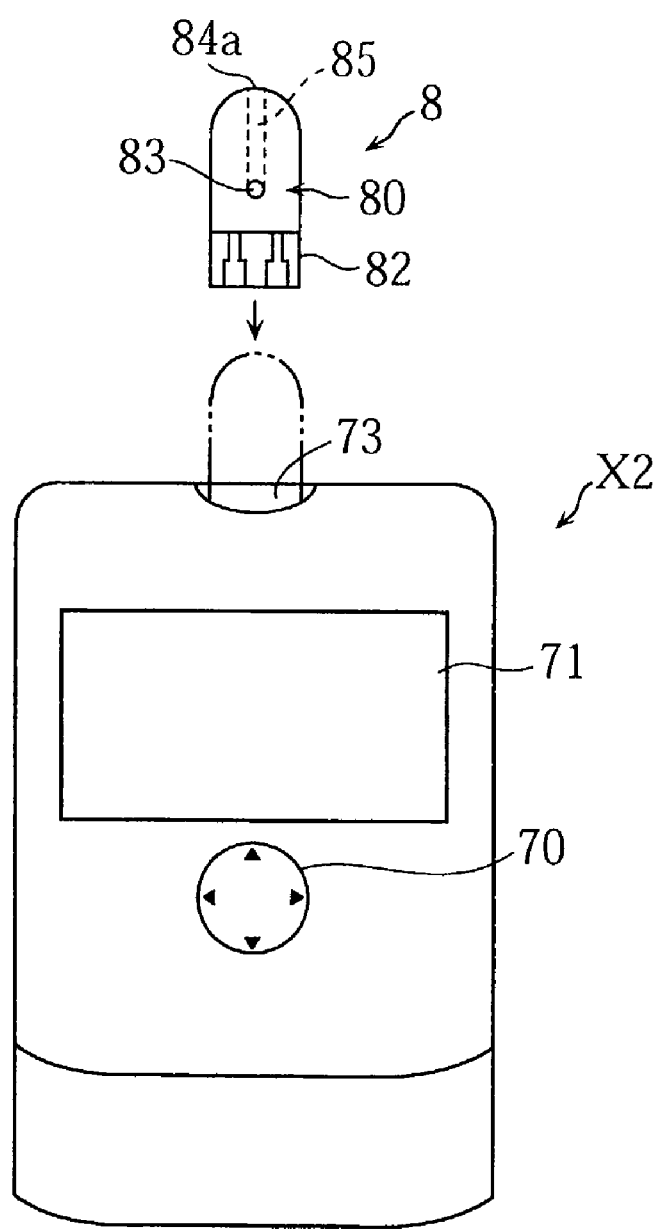
FIG. 10 is a front view showing one example of an analyzer and biosensor (test piece) of a second embodiment of this invention.

The analyzer X2 shown in FIG. 10 computes the concentration of a specific component in a sample liquid from the value of the current flowing when a constant voltage is applied.

The sample liquid may be, for example, blood or other biological samples, or liquids obtained by adjusting same. Specific components may be, for example, glucose or cholesterol.

Figure 11:
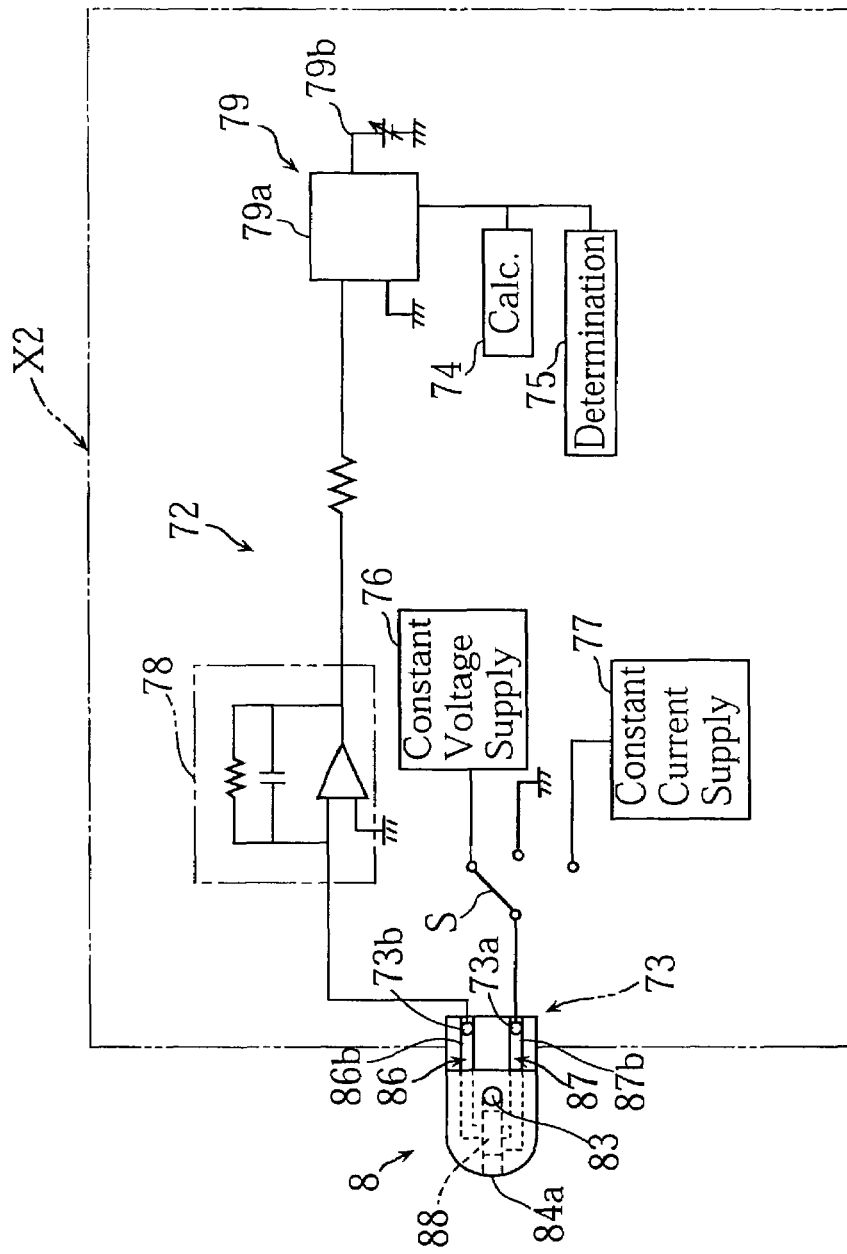
FIG. 11 is a schematic view mainly showing a circuit for response current measurement, when a biosensor is set in the analyzer of FIG. 10.

The analyzer X2 comprises an operating button 70, and a display 71 to display measurement results, as shown in FIGS. 10 and 11. This analyzer X2 has a response current measurement circuit 72, set portion 73, computation portion 74, and determination portion 75.

The response current measurement circuit 72 has a constant voltage supply portion 76, constant current supply portion 77, amplifier portion 78, and current value measurement instrument 79.

The constant voltage supply portion 76 provides a constant voltage to the biosensor 8 during measurements of the concentration of the specific component. The constant current supply portion 77 supplies a constant current to the test piece 8' (see FIG. 14) during test of the response current measurement circuit 72. The state in which the constant voltage supply portion 76 or constant current supply portion 77 is connected to the biosensor 8 or test piece 8' is selected by turning the analog switch S on and off. The analog switch S can also select the state in which the test piece 8' is grounded. Hence by switching the analog switch, a plurality of standard currents can be supplied to the test piece 8'.

The current value measurement instrument 79 has, for example, an A/D converter 79a capable of current measurements, and a knob-operated regulator 79b which performs calibration of the A/D converter 79a.

The set portion 73 is the location in which the biosensor 8 is installed as the test piece. This set portion 73 is provided with measurement probes 73a, 73b to make contact with the terminal portions 86b, 87b of the biosensor 8.

The computation portion 74 computes the concentration of the specific component based on the current value measured by the A/D converter 79a. This computation portion

74 has, for example, a CPU, ROM, and RAM. Working curve data indicating the relation between the concentration of each specific component and the response current value, and a program to compute the concentration of a specific component by applying measured current values to the working curve data, are stored in the ROM.

The determination portion 75 judges whether there is a defect in the potential difference measurement circuit 6. The determination portion 75 has, for example, a CPU, ROM, and RAM. The ROM stores, for example, ideal response current values for each standard current, and a program which compares response current values actually measured by the A/D converter 79*a* for each standard current, and judges whether there is a defect in the response current measurement circuit 72.

The computation portion 74 and determination portion 75 may be configured so as to share the CPU and RAM.

Figure 12:
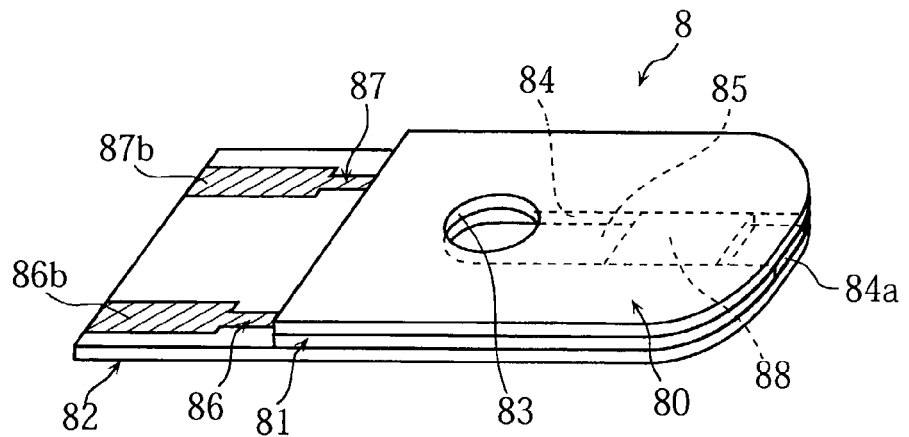
FIG. 12 is an overall perspective view showing one example of a biosensor.
Figure 13:
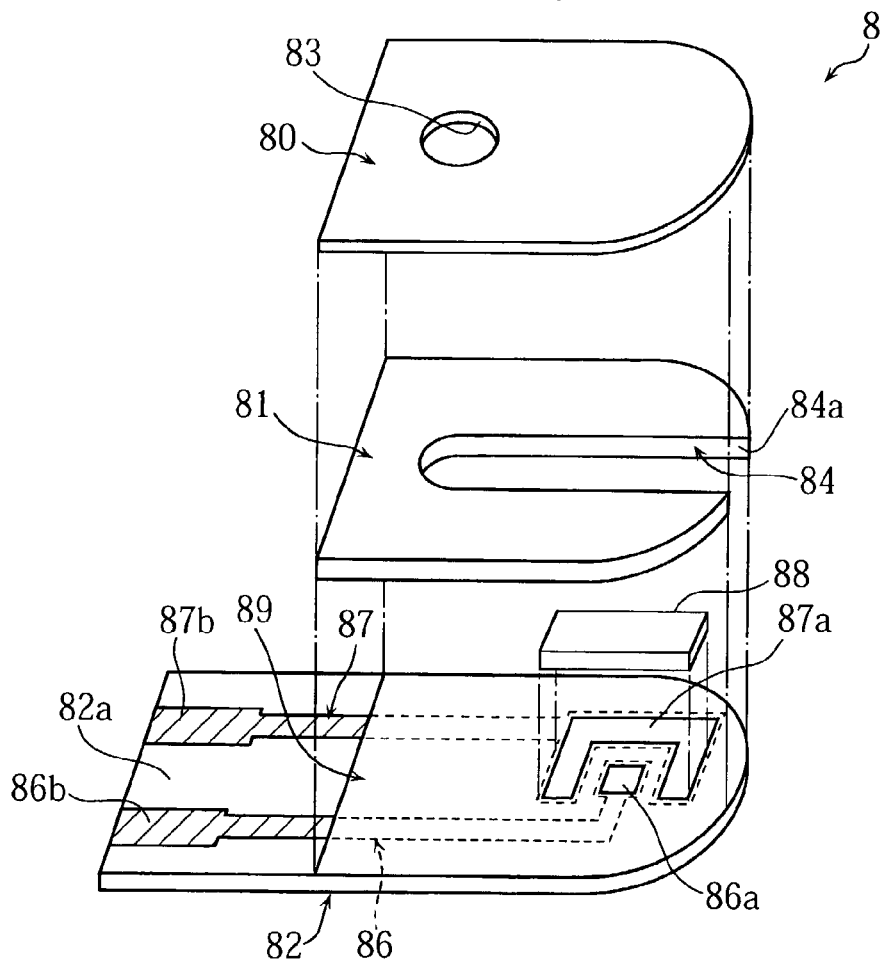
FIG. 13 is an exploded perspective view of the biosensor of FIG. 12.

As clearly shown in FIGS. 12 and 13, the biosensor 8 has a cover plate 80, spacer 81, and base 82 in a stacked configuration.

The cover plate 80 is provided with a hole 83. The spacer 81 is provided with a narrow slit 84, the tip of which is open. This slit 84 is linked with the hole 83. By means of the slit 84, a passage 85 between the cover plate 80 and base 82 is formed. This passage 85 is linked with the exterior via the open tip portion 84*a* of the slit 84 and the hole 83. The open tip portion 84*a* is an opening for the introduction of sample liquid; the hole 83 is a vent hole to vent gas in the passage 85. Hence a sample liquid supplied from the introductory opening (open tip portion) 84*a* proceeds through the passage 85 toward the hole (vent hole) by means of the capillary action effect.

A pair of electrodes 86, 87 and a reaction portion 88 are provided on the upper face 82*a* of the base 82.

The electrodes 86, 87 are covered by an insulating film 89 such that tips at one end 86*a*, 87*a* and tips at the other end 86*b*, 87*b* are exposed. The tip at one end 86*a* of the electrode 86 is a rectangular pad exposing a rectangular area. The tip at one end 87*a* of the electrode 87 is a "U"-shaped pad with a "U"-shaped area exposed, surrounding three sides of the rectangular pad 86*a*. On the other hand, the other tips 86*b*, 87*b* of these electrodes 86, 87 are terminal portions which are electrically connected to the measurement terminals 73*a*, 73*b* of the analyzer X2.

The reaction portion 88 is, for example, a solid shape, provided so as to bridge the interval between the rectangular pad 86*a* and the "U"-shaped pad 87*a*. This reaction portion 88 comprises, for example, an oxidation-reduction enzyme and an electron acceptor. As the oxidation-reduction enzyme, for example, glucose oxidase, which oxidizes glucose in the blood to gluconic acid and reduces electron acceptors, is used. On the other hand, potassium ferricyanide is for example used as the electron acceptor.

The biosensor 8 is set in the set portion 73 of the analyzer X2, and the terminal portions 86*b*, 87*b* are electrically connected with the measurement probes 73*a*, 73*b* of the analyzer X2.

A sample liquid introduced from the introductory opening 84*a* of the biosensor 8 proceeds within the passage 85 through capillary action. In this process, the sample liquid dissolves the reaction portion 88. At this time, electrons are removed from the specific component in the sample by the oxidation-reduction enzyme, the specific component is oxidized, and the electrons are supplied to the electron acceptor, thereby reducing the electron acceptor. If a constant voltage is applied by the constant voltage supply portion 76 (see FIG. 11) across the terminal portions 86*a*, 87*a* after a fixed amount of time from the introduction of the sample liquid, electrons accepted by the electron acceptor are emitted from the electron acceptor.

As shown in FIG. 11, electrons emitted from the electron acceptor (the output) are amplified by the amplifier portion 78, and the result is input to the current value measurement instrument 79. In this current value measurement instrument 79, the response current value after, for example, a fixed length of time has elapsed from the start of application of the constant voltage is measured.

The concentration of the specific component is computed by the computation portion 74 from the measured current value. The computation result is, for example, displayed on the display 71 (see FIG. 10).

Figure 14:
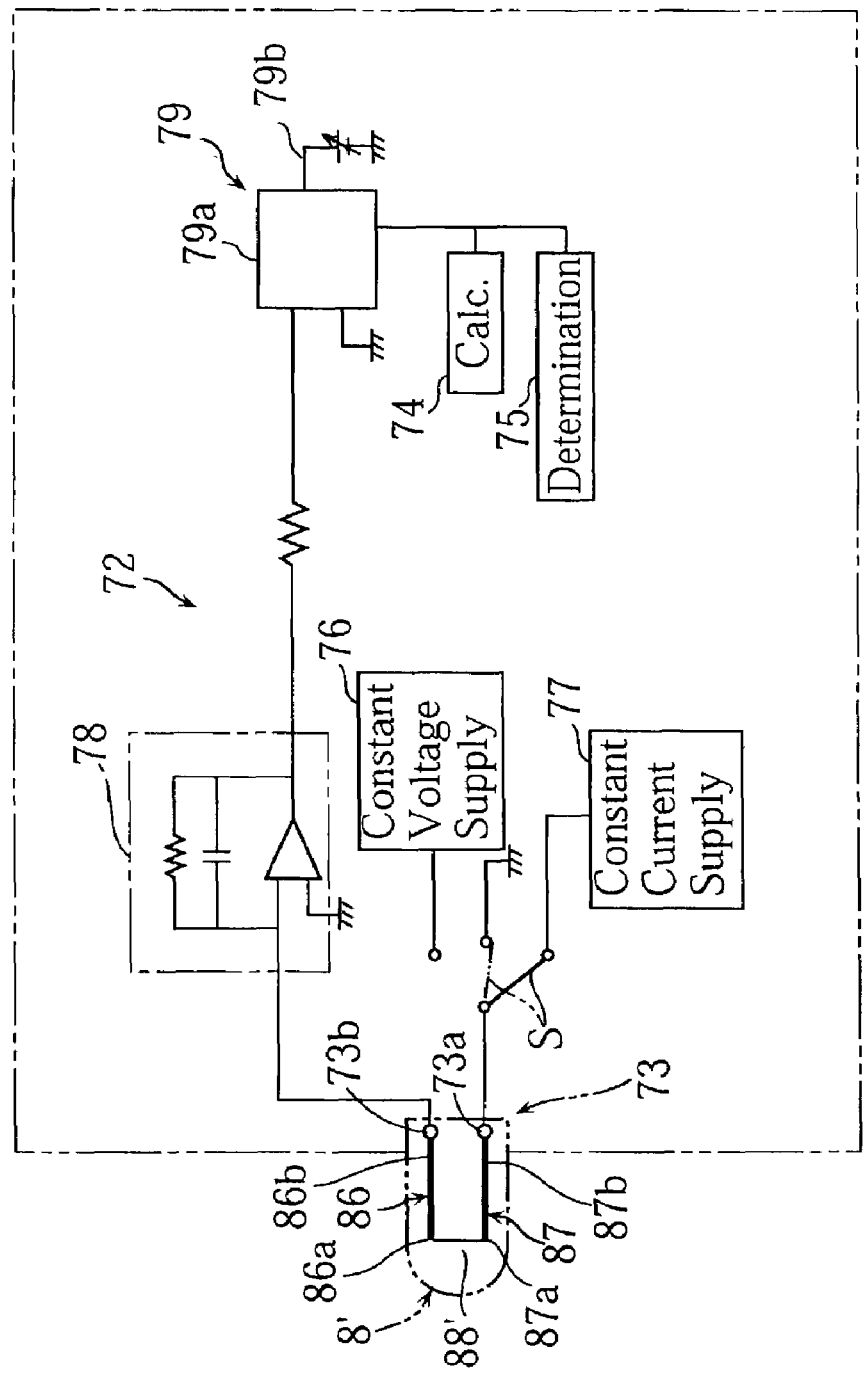
FIG. 14 is a schematic view mainly showing a circuit for response current measurement, when a check piece is set in the analyzer.
Figure 15:
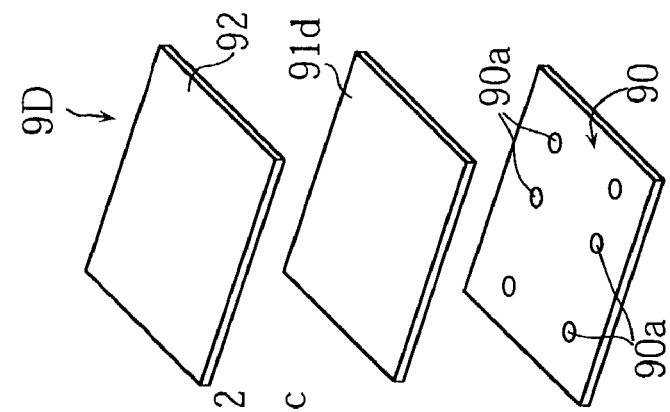
FIG. 15 is an exploded perspective view showing one example of a conventional check piece.
Figure 16:
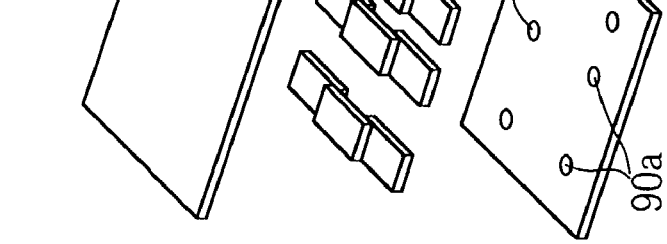
FIG. 16 is an exploded perspective view showing another example of a conventional check piece.
Figure 17:
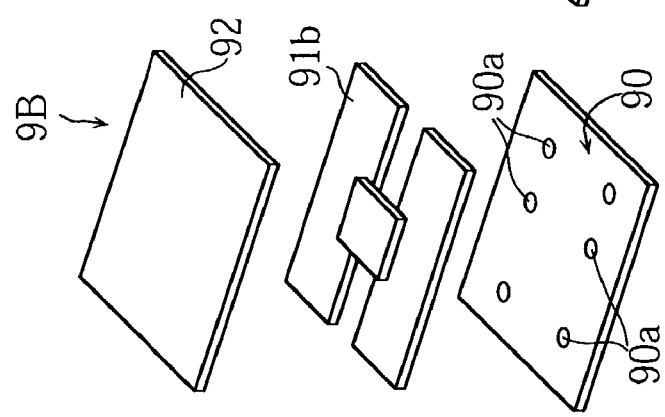
FIG. 17 is an exploded perspective view showing another example of a conventional check piece.
Figure 18:
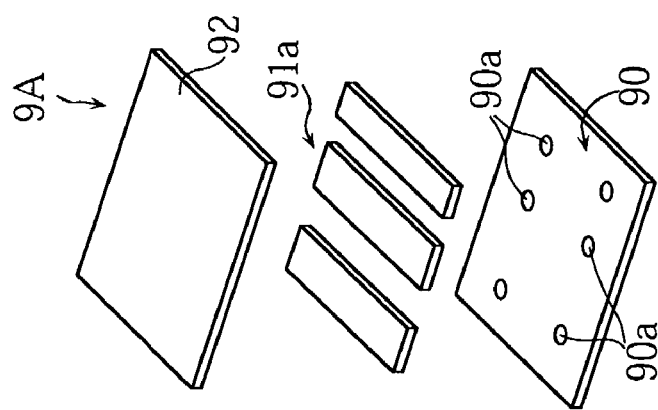
FIG. 18 is an exploded perspective view showing another example of a conventional check piece.
Figure 19:
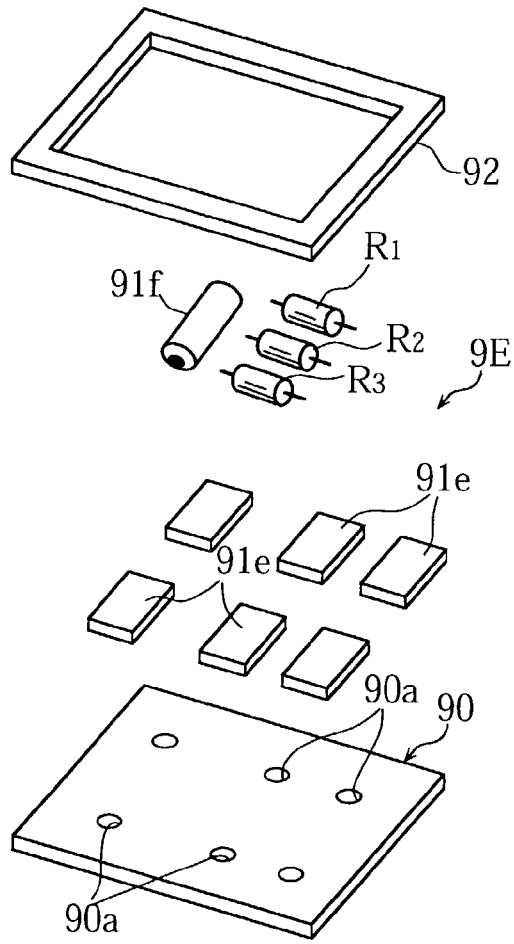
FIG. 19 is an exploded perspective view showing another example of a conventional check piece.
Figure 20:
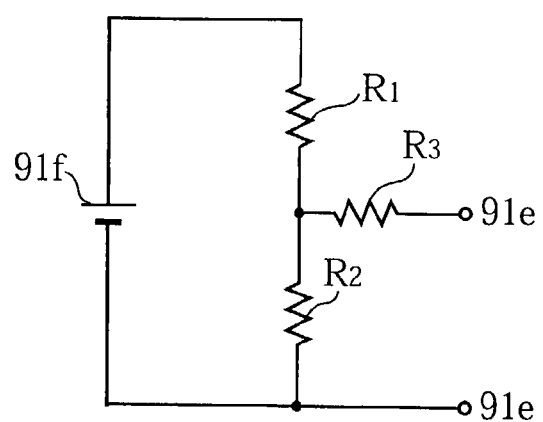
FIG. 20 is a circuit diagram of the check piece of FIG. 19.

In the analyzer X2, by setting a check piece 8' in the set portion 73 in place of the biosensor 8, as shown in FIG. 14, the response current measurement circuit 72 can be tested. In this test, damage to the electronic components and breakage of wiring comprised by the response current measurement circuit 72, as well as contract failure between measurement probes 73*a*, 73*b* and the check piece 8' (biosensor 8), can be investigated.

The check plate 8' has a conductor 88', for example, positioned to correspond to the reaction portion 88 of the biosensor 8. Hence with the check plate 8' set in the set portion 73 of the analyzer X2, the response current measurement circuit 72 becomes the circuit shown in FIG. 14.

In tests of the response current measurement circuit 72, the analog switch S is switched to connect the terminal portion 87*b* of the check piece 8' with the constant current supply portion 77, in order to supply a constant current (standard current) to the check piece 8'. The standard current value is, for example, 10 µA.

The output from the check piece 8' is amplified by the amplifier portion 78 and is then input to the current value measurement instrument 79. In the current value measurement instrument 79, the response current value is measured by the A/D converter 79*a*.

In the determination portion 75, the response current value measured by the A/D converter 79*a* is compared with the ideal response current value obtained when a standard current is supplied to the check piece 8', to judge whether the response current measurement circuit 72 is normal or not.

The response current measurement circuit 72 is configured such that, ideally, the standard current supplied to the check piece 8' is measured by the A/D converter 79*a*. Hence when the response current value measured by the A/D converter 79*a* deviates from the standard current, exceeding a tolerance range, the determination portion 75 judges that an abnormality has occurred in the response current measurement circuit 72.

Next, the analog switch S is switched to ground the terminal portion 87*b* of the check piece 8', setting the standard current value to zero. At this time, if the response current value measured by the current value measurement instrument 79 deviates greatly from zero, the determination portion 75 judges that an abnormality has occurred in the response current measurement circuit 72.

On the other hand, when two different standard currents are supplied to the check piece 8' and the response currents measured by the A/D converter 79*a* agree, or substantially agree, with the corresponding standard currents, the determination portion 75 judges that the response current measurement circuit 72 is normal.

In the second embodiment of the invention also, the current value measurement instrument 79 may be connected to the constant current supply portion 77, and the knob-operated regulator 79b used to calibrate the A/D converter 79a, after which response current values are measured.

In the analyzers X1, X2, rather than performing electrical tests of the measurement electrical circuit using a single standard voltage, as in the prior art, tests of the measurement electrical circuits 6, 72 are performed based on a plurality of electrical conditions, as explained referring to FIGS. 9 and 14. Even in cases in which a measurement of the response for a single electrical condition results in a small difference between the response and the electrical condition, so that a judgment of normality is not possible, if measurements are performed for a plurality of electrical conditions, a large difference with the response may appear for one of the electrical conditions. Hence if the responses for each of the electrical conditions are considered in combination, it is possible to perform tests for defects in the measurement electrical circuits 6, 72 with greater reliability.

Further, if tests are performed for a plurality of electrical conditions, the linearity of a plot of the responses can provide a better understanding of whether the measurement precision is sufficient within the range of the plurality of electrical conditions.

In the analyzer X1 of the first embodiment of this invention, as explained in reference to FIG. 9, a step is included in which, prior to applying a standard voltage to the check plate 4', a standard voltage is applied to the A/D converter 63a to calibrate the A/D converter 63a. By performing this calibration, the potential difference measurement circuit 6 can be reliably tested for defects even if the standard voltage supplied to the check plate 4' is not the desired value, and even if error occurs in the measurement value of the A/D converter 63a.

An analyzer of this invention may be configured such that, after a test piece set in the set portion has been drawn into the device, potential differences and current values are measured in the device interior.

An analyzer of this invention may be configured such that a check plate is incorporated in advance into the interior of the analyzer, so that by selecting an test mode, tests of the measurement electrical circuit are performed automatically using the check plate.

It is sufficient to set a plurality of electrical conditions, without being limited to the three conditions +100 mV, 0V, −100 mV of the first embodiment of this invention, or to the conditions 10 μA and 0A of the second embodiment of this invention. The number of electrical condition settings and the values of same are a matter of design.

This invention places no limits in particular on the number or types of specific components to be measured by the analyzer.

The invention claimed is:

1. An analysis system comprising an analyzer and a check piece used for checking workings of the analyzer, the analyzer utilizing a test piece that includes a first terminal portion and a second terminal portion for measuring a concentration of a specific component in a sample liquid supplied to the test piece, the analyzer comprising: a set portion in which the test piece is set; a first measurement terminal for electrical connection to the first terminal portion; a second measurement terminal for electrical connection to the second terminal portion; a measurement electrical circuit to measure electrical physical quantities generated by the sample liquid in accordance with the concentration of the specific component; and a variable physical quantity output unit for supplying trial physical quantities for checking working of the measurement electrical circuit;

wherein the electrical physical quantities are voltages, the trial physical quantities including a plurality of standard voltages, the variable physical quantity output unit being a constant-voltage power supply which can change an output level, the measurement electrical circuit serving to measure a voltage of the first measurement terminal;

wherein the set portion is configured to receive die check piece instead of the test piece, the check piece being used for conducting the checking of the working of the measurement electrical circuit, wherein upon setting the check piece in the set portion, an electrical path extending in the measurement electrical circuit and the check piece is made, so that an output of the variable physical quantity output unit can be conducted to at least one of the first measurement terminal and the second measurement terminal, then through the check piece, and back to the measurement electrical circuit.

2. The system according to claim 1, wherein the analyzer further comprises a determination portion for judging whether there is a defect in the measurement electrical circuit by comparing an actual electrical response from the measurement electrical circuit with an ideal electrical response.

3. The system according to claim 1, wherein the analyzer is configured to measure a potential difference arising between a reference liquid having a known concentration of the specific component and the sample liquid having an unknown concentration of the specific component.

4. The system according to claim 3, wherein the check piece has a first conducting portion for contact with the first measurement terminal and a second conducting portion for contact with the second measurement terminal, the first conducting portion and the second conducting portion being electrically insulated from each other when the check piece is not set in the set portion.

5. The system according to claim 4, wherein the plurality of standard voltages comprise at least two of a positive value, zero, and a negative value.

6. The system according to claim 5, wherein at least one of the plurality of standard voltages is applied by connecting a power supply to the first conducting portion while grounding the second conducting portion.

7. The system according to claim 6, wherein the voltage of the power supply is controlled by a regulator within the analyzer.

8. The system according to claim 1, wherein the measurement electrical circuit has a response measurement instrument to measure the electrical responses, the response measurement instrument being calibrated by applying electrical physical quantities to the response measurement instrument.

9. The system according to claim 1, wherein the check piece is incorporated into the analyzer from outside at the time of performing the checking of the measurement electrical circuit.

10. The system according to claim 1, wherein the check piece is incorporated into the analyzer in advance.

11. An analysis system comprising an analyzer and a check piece used for checking workings of the analyzer, the analyzer utilizing a test piece that includes a first terminal portion and a second terminal portion for measuring a concentration of a specific component in a sample liquid supplied to the test piece, the analyzer comprising; a set portion in which the test piece is set; a first measurement terminal for electrical connection to the first terminal portion; a second measurement terminal for electrical connection to the second terminal portion; a measurement electrical circuit to measure electrical physical quantities generated by the sample liquid in accordance with the concentration of the specific component; and a variable physical quantity output unit for supplying trial physical quantities for checking working of the measurement electrical circuit;

wherein the electrical physical quantities are currents, the trial physical quantities including a plurality of standard currents, the variable physical quantity output unit being a constant-current power supply which can change an output level, the measurement electrical circuit serving to measure a current of the first measurement terminal;

wherein the set portion is configured to receive the check piece instead of the test piece, the check piece being used for conducting the checking of the working of the measurement electrical circuit, wherein upon setting the check piece in the set portion, an electrical path extending in the measurement electrical circuit and the cheek piece is made, so that an output of the variable physical quantity output unit can be conducted to at least one of the first measurement terminal and the second measurement terminal, then through the check piece, and back to the measurement electrical circuit.

12. The system according to claim 11, wherein the check piece has a first conducting portion for contact with the first measurement terminal and a second conducting portion for contact with the second measurement terminal, the first conducting portion and the second conducting portion being electrically connected.

13. The system according to claim 11, wherein the plurality of standard currents are positive or zero.

14. A method of testing an analyzer utilizing a test piece that includes a first terminal portion and a second terminal portion for measuring a concentration of a specific component in a sample liquid supplied to the test piece; the analyzer comprising: a set portion in which the test piece is set; a first measurement terminal for electrical connection to the first terminal portion; a second measurement terminal for electrical connection to the second terminal portion; a measurement electrical circuit which measures electrical physical quantities generated by the sample liquid in accordance with the concentration of the specific component; and a variable physical quantity output unit for supplying trial physical quantities for checking working of the measurement electrical circuit;

wherein the electrical physical quantities are voltages, the trial physical quantities including a plurality of standard voltages, the variable physical quantity output unit being a constant-voltage power supply which can change an output level, the measurement electrical circuit serving to measure a voltage of the first measurement terminal;

the method comprising:

a preliminary step for setting a check piece instead of the test piece in the set portion to make an electrical path extending in the measurement electrical circuit and the check piece, so that an output of the variable physical quantity output unit can be conducted to at least one of the first measurement terminal and the second measurement terminal, then through the check piece, and back to the measurement electrical circuit;

a first step for applying a trial physical quantity to the check piece;

a second step for measuring an electrical response obtained from the measurement electrical circuit upon application of the trial physical quantity; and a third step for comparing the electrical response with an ideal electrical response obtainable when a physical quantity is applied to the check piece;

wherein the first through third steps are performed separately for each of a the plurality of standard voltages.

15. The method according to claim 14, wherein the measurement electrical circuit has a response measurement instrument far measuring the elemental response, the method further comprising, prior to first performance of the first step, a step for applying electrical physical quantities to the response measurement instrument and calibrating the response measurement instrument.

16. A method of testing an analyzer utilizing a test piece that includes a first terminal portion and a second terminal portion for measuring a concentration of a specific component in a sample liquid supplied to the test piece; the analyzer comprising: a set portion in which the test piece is set; a first measurement terminal for electrical connection to the first terminal portion; a second measurement terminal for electrical connection to the second terminal portion; a measurement electrical circuit which measures a current of the first measurement terminal generated by the sample liquid in accordance with the concentration of the specific component; and a constant-current power supply which can change an output level and supplies trial physical quantities for checking working of the measurement electrical circuit, the trial physical quantities including a plurality of standard currents;

the method comprising:

a preliminary step for setting a cheek piece instead of the test piece in the set portion to make an electrical path extending in the measurement electrical circuit and the check piece, so that an output of the variable physical quantity output unit can be conducted to at least one of the first measurement terminal and the second measurement terminal, then through the check piece, and back to the measurement electrical circuit;

a first step for applying a trial physical quantity to the check piece;

a second step for measuring an electrical response obtained from the measurement electrical circuit upon application of the trial physical quantity; and a third step for comparing the electrical response with an ideal electrical response obtainable when a physical quantity is applied to the check piece;

wherein the first through third steps are performed separately for each of the plurality of standard currents.

* * * * *